United States Patent
Harris et al.

(10) Patent No.: US 10,111,770 B2
(45) Date of Patent: *Oct. 30, 2018

(54) METHODS AND DEVICES FOR ACTIVATING BROWN ADIPOSE TISSUE WITH TARGETED SUBSTANCE DELIVERY

(71) Applicants: Ethicon Endo-Surgery, Inc., Cincinnati, OH (US); The General Hospital Corporation, Boston, MA (US)

(72) Inventors: Jason L. Harris, Lebanon, OH (US); Taylor W. Aronhalt, Loveland, OH (US); Dwight Henninger, Waynesville, OH (US); James W. Voegele, Cincinnati, OH (US); Lee M. Kaplan, Wellesley, MA (US); Nicholas Stylopoulos, Swampscott, MA (US)

(73) Assignees: Ethicon Endo-Surgery, Inc., Cincinnati, OH (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/438,202

(22) Filed: Feb. 21, 2017

(65) Prior Publication Data

US 2017/0156907 A1    Jun. 8, 2017

Related U.S. Application Data

(63) Continuation of application No. 13/977,501, filed as application No. PCT/US2011/066399 on Dec. 21, 2011, now Pat. No. 9,610,429.

(60) Provisional application No. 61/427,991, filed on Dec. 29, 2010.

(51) Int. Cl.
| | | |
|---|---|---|
| *A61M 5/00* | (2006.01) | |
| *A61K 9/70* | (2006.01) | |
| *A61F 5/00* | (2006.01) | |
| *A61M 5/142* | (2006.01) | |
| *A61M 5/14* | (2006.01) | |
| *A61M 35/00* | (2006.01) | |
| *A61K 9/00* | (2006.01) | |
| *A61M 37/00* | (2006.01) | |
| *A61M 5/172* | (2006.01) | |

(52) U.S. Cl.
CPC .......... *A61F 5/0003* (2013.01); *A61K 9/0014* (2013.01); *A61K 9/0019* (2013.01); *A61K 9/7023* (2013.01); *A61M 5/14* (2013.01); *A61M 5/14276* (2013.01); *A61M 35/00* (2013.01); *A61M 37/00* (2013.01); *H05K 999/99* (2013.01); *A61M 2005/1726* (2013.01); *A61M 2205/50* (2013.01); *A61M 2230/06* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 4,498,843 A | 2/1985 | Schneider et al. | |
| 4,978,338 A | 12/1990 | Melsky et al. | |
| 5,422,352 A * | 6/1995 | Astrup ................. | A61K 31/475 514/263.31 |
| 6,072,100 A | 6/2000 | Mooney et al. | |
| 6,532,386 B2 | 3/2003 | Sun et al. | |
| 6,645,229 B2 | 11/2003 | Matsumura et al. | |
| 6,922,590 B1 | 7/2005 | Whitehurst | |
| 7,191,007 B2 | 3/2007 | Desai et al. | |
| 7,300,409 B2 | 11/2007 | Kopanic, Jr. et al. | |
| 7,599,743 B2 | 10/2009 | Hassler, Jr. et al. | |
| 7,599,744 B2 | 10/2009 | Giordano et al. | |
| 7,735,073 B1 | 6/2010 | Kosche et al. | |
| 7,970,478 B2 | 6/2011 | Wahlgren et al. | |
| 8,126,530 B2 | 2/2012 | Bare et al. | |
| 8,303,982 B2 | 11/2012 | Smith et al. | |
| 9,610,429 B2 | 4/2017 | Harris et al. | |
| 2005/0177067 A1 | 8/2005 | Tracey et al. | |
| 2005/0277998 A1 | 12/2005 | Tracey et al. | |
| 2005/0288740 A1 | 12/2005 | Hassler et al. | |
| 2006/0195146 A1 | 8/2006 | Tracey et al. | |
| 2006/0195153 A1 | 8/2006 | DiUbaldi et al. | |
| 2007/0100387 A1 | 5/2007 | Gerber | |
| 2007/0154538 A1 | 7/2007 | Neuberger et al. | |

(Continued)

FOREIGN PATENT DOCUMENTS

WO    WO-8911701 A1    11/1989

OTHER PUBLICATIONS

[No Author Listed] 3M CoTran 9702 Membrane: Controlled Caliper Ethylene Vinyl Acetate (EVA) Membrane. Product data sheet. 2009, 2 pages.

(Continued)

*Primary Examiner* — Jessica Worsham
(74) *Attorney, Agent, or Firm* — Mintz Levin Cohn Ferris Glovsky and Popeo, P.C.

(57) ABSTRACT

Methods and devices are provided for activating brown adipose tissue with targeted substance delivery. Generally, the methods and devices can activate BAT to increase thermogenesis, e.g., increase heat production in the patient, which over time can lead to weight loss and/or improved metabolic function. In one embodiment, a chemical configured to stimulate nerves that activate the BAT and/or to stimulate brown adipocytes directly can be delivered to a patient, thereby increasing thermogenesis in the BAT and inducing weight loss and/or improved metabolic function through energy expenditure. The chemical can be delivered to the patient locally and/or systemically to stimulate the nerves and/or the brown adipocytes.

13 Claims, 3 Drawing Sheets

(56) References Cited

U.S. PATENT DOCUMENTS

| | | |
|---|---|---|
| 2007/0185541 A1 | 8/2007 | DiUbaldi et al. |
| 2008/0132962 A1 | 6/2008 | DiUbaldi et al. |
| 2008/0139875 A1 | 6/2008 | Tracey et al. |
| 2008/0147146 A1 | 6/2008 | Wahlgren et al. |
| 2009/0018594 A1 | 1/2009 | Laufer et al. |
| 2009/0093858 A1 | 4/2009 | DiUbaldi |
| 2009/0132018 A1 | 5/2009 | DiUbaldi et al. |
| 2009/0149918 A1 | 6/2009 | Krulevitch et al. |
| 2009/0157149 A1 | 6/2009 | Wahlgren et al. |
| 2009/0171375 A1 | 7/2009 | Coe et al. |
| 2009/0202387 A1 | 8/2009 | Dlugos, Jr. et al. |
| 2009/0204131 A1 | 8/2009 | Ortiz et al. |
| 2010/0161001 A1 | 6/2010 | DiUbaldi et al. |
| 2010/0249677 A1 | 9/2010 | DiUbaldi et al. |
| 2010/0312295 A1 | 12/2010 | Vase et al. |
| 2011/0270360 A1 | 11/2011 | Harris et al. |
| 2012/0165792 A1 | 6/2012 | Ortiz et al. |
| 2012/0172783 A1 | 7/2012 | Harris et al. |
| 2012/0172792 A1 | 7/2012 | Baynham et al. |
| 2014/0018767 A1 | 1/2014 | Harris et al. |

OTHER PUBLICATIONS

[No Author Listed] 3M CoTran 9705 Membrane: Controlled Caliper Ethylene Vinyl Acetate (EVA) Membrane. Product data sheet. 2009, 2 pages.

[No Author Listed] 3M CoTran 9706 Membrane: Controlled Caliper Ethylene Vinyl Acetate (EVA) Membrane. Product data sheet. 2009, 2 pages.

[No Author Listed] 3M CoTran 9707 Membrane: Controlled Caliper Ethylene Vinyl Acetate (EVA) Membrane. Product data sheet. 2009, 2 pages.

[No Author Listed] 3M CoTran 9712 Membrane: Controlled Caliper Ethylene Vinyl Acetate (EVA) Membrane. Product data sheet. 2009, 2 pages.

[No Author Listed] 3M CoTran 9715 Membrane: Controlled Caliper Ethylene Vinyl Acetate (EVA) Membrane. Product data sheet. 2009, 2 pages.

[No Author Listed] 3M CoTran 9716 Membrane: Controlled Caliper Ethylene Vinyl Acetate (EVA) Membrane. Product data sheet. 2009, 2 pages.

[No Author Listed] 3M CoTran 9728 Membrane: Controlled Caliper Ethylene Vinyl Acetate (EVA) Membrane. Product data sheet. 2009, 2 pages.

[No Author Listed] Researchers Turn to Silver Nanoparticles to Reinvent Implantable-Device Batteries. Medtechinsider. Retrieved from <http://medtechinsider.com/archives/12240>. Feb. 11, 2010, 4 pages.

[No Author Listed] Solicore Product Matrix. Retrieved from <http://www.solicore.com/product-matrix.asp> on May 11, 2011. Revised Jan. 2007. 1 page.

[No Author Listed] Transdermal Technologies, Membranes: 3M CoTran Membranes. Retrieved from <http://solutions.3m.com>. 2010, 5 pages.

Bartlet et al., Brown adipose tissue activity controls triglyceride clearance. Nature Medicine. 2011;17:200-205. Supplemental information included.

Cannon et al., Brown adipose tissue: function and physiological significance. Physiol Rev. 2004;84:277-359.

Heaton, J.M., The distribution of brown adipose tissue in the human. J Anat. 1972;112(1):35-39.

International Search Report and Written Opinion for Application No. PCT/US2011/66399, dated Apr. 26, 2012 (10 Pages).

International Preliminary Report on Patentability for Application No. PCT/US2011/066399, dated Jul. 11, 2013 (6 pages).

Lever et al., Demonstration of a catecholaminergic innervation in human perirenal brown adipose tissue at various ages in the adult. Anat Rec. 1986;215(3):251-5.

Rothwell et al., A role for brown adipose tissue in diet-induced thermogenesis. Nature. 1979;281(5726):31-5.

Shimizu, et al., Sympathetic activation of glucose utilization in brown adipose tissue in rats. J Biochem. 1991;110:688-692.

Stylopoulos et al., Roux-en-Y gastric bypass enhances energy expenditure and extends lifespan in diet-induced obese rats. Obesity. 2009;17:1839-47.

Tajino et al., Application of menthol to the skin of whole trunk in mice induces automatic and behavioral heat-gain responses. Am J Physiol Regul Integr Comp Physiol. 2007;293:R2128-35. Epub Aug. 29, 2007.

van Marken Lichtenbelt et al., Cold-activated brown adipose tissue in healthy men. N Engl J Med. 2009;360:1500-1508.

Virtanen et al., Functional brown adipose tissue in healthy adults. The New England Journal of Medicine. 2009;360(15):1518-1525.

* cited by examiner

METHODS AND DEVICES FOR ACTIVATING BROWN ADIPOSE TISSUE WITH TARGETED SUBSTANCE DELIVERY

CROSS REFERENCE TO RELATED APPLICATIONS

The present application claims priority to U.S. patent application Ser. No. 13/977,501 entitled "Methods And Devices For Activating Brown Adipose Tissue With Targeted Substance Delivery" filed Jun. 28, 2013, which claims priority to International Application No. PCT/US11/66399 entitled "Methods And Devices For Activating Brown Adipose Tissue With Targeted Substance Delivery" filed Dec. 21, 2011, which claims priority to U.S. Provisional Patent Application No. 61/427,991 entitled "Methods And Devices For Activating Brown Adipose Tissue With Targeted Substance Delivery" filed Dec. 29, 2010, which are hereby incorporated by reference herein in their entireties.

FIELD OF THE INVENTION

The present invention relates to methods and devices for inducing weight loss and/or improved metabolic function, and in particular to methods and devices for activating brown adipose tissue.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure and/or altering a patient's metabolism, e.g., a basal metabolic rate, leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity and in particular for activating BAT.

SUMMARY OF THE INVENTION

The present invention generally provides methods and devices for activating brown adipose tissue with targeted substance delivery. In one embodiment, a medical method is provided that includes positioning a device in contact with tissue of a patient proximate to a receptor in communication with at least a portion of a depot of brown adipose tissue, and activating the device to deliver a chemical to the patient to activate the brown adipose tissue and increase energy expenditure of the brown adipose tissue. The depot of brown adipose tissue can be located anywhere, such as in a supraclavicular region of the patient.

The chemical can have a variety of configurations. For example, the chemical can be configured to chemically interact with cellular surface receptors of the brown adipose tissue. For another example, the chemical can include menthol.

The chemical can be delivered to the patient in a variety of ways. In one embodiment, the chemical can be continuously delivered to the patient for a predetermined amount of time, e.g., at least four weeks. The device can be configured to be in continuous direct contact with the tissue of the patient for at least one day with the device continuously delivering the chemical to the patient for at least one day.

In one embodiment, the method can include delivering a second chemical to the patient. The chemical can be configured to respond to the second chemical when the chemical is exposed to the second chemical, the response of the chemical causing activation of the brown adipose tissue. The chemical can be configured to be active in the patient when the chemical is exposed to the second chemical, and can be configured to be inert in the patient when the chemical is not exposed to the second chemical. Delivering the second chemical to the patient can include alternating at least once between delivering the second chemical to the patient during a first period of time and not delivering the second chemical to the patient during a second period of time.

The method can include positioning a second device in contact with tissue of the patient proximate to a receptor in communication with at least a portion of another depot of brown adipose tissue, and activating the second device to deliver a second chemical to the patient to activate the other depot of brown adipose tissue and increase energy expenditure of the other depot of brown adipose tissue. The second device can deliver the second chemical to the patient simultaneously with the device delivering the chemical to the patient.

The device can be activated in response to a trigger event including at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device. The device can be activated to deliver the chemical to the patient to activate the brown adipose tissue without cooling the patient or the brown adipose tissue.

Positioning the device in contact with tissue of the patient proximate to a receptor in communication with at least a portion of a depot of brown adipose tissue can include positioning the device proximate to at least one of a supraclavicular region, a nape of a neck, a scapula, a spinal cord, proximal branches of the sympathetic nervous system that terminate in BAT depots, a kidney, the brain, and the gut.

The method can vary in any number of ways. For example, the method can include targeting the chemical to a nerve innervating the brown adipose tissue to activate the brown adipose tissue. For another example, delivering the chemical to the patient can include applying the chemical to an exterior surface of skin proximate to the depot of brown adipose tissue. For yet another example, positioning the device in contact with tissue of the patient can include transcutaneously applying the device to an exterior skin surface of the patient or subcutaneously positioning at least a portion of the device within the patient. Subcutaneously positioning at least a portion of the device within the patient can include implanting the device entirely within the patient. For still another example, the method can include reducing an amount of the chemical delivered to the patient over a predetermined period of time until a first predetermined threshold event occurs, and subsequently increasing the amount of the chemical delivered to the patient over the predetermined period until a second predetermined threshold event occurs. For another example, the method can include imaging the patient to locate the depot of brown adipose tissue prior to positioning the device in contact with tissue of the patient proximate to the depot of brown adipose tissue.

For another example, the method can include stopping delivery of the chemical, waiting a predetermined amount of time, and activating the device to deliver an additional amount of the chemical to the patient to activate the depot of brown adipose tissue and increase energy expenditure of the brown adipose tissue. The stopping, the waiting, and the activating can be repeated until occurrence of a threshold event. The threshold event can include at least one of a predetermined amount of time and a predetermined physiological effect.

For yet another example, the method can include removing the device from the patient, repositioning the device in contact with tissue of the patient proximate to a receptor in communication with at least a portion of another depot of brown adipose tissue, and activating the device proximate to the other depot of brown adipose tissue to deliver the chemical to the patient to activate the other depot of brown adipose tissue and increase energy expenditure of the other depot of brown adipose tissue. The depot of brown adipose tissue can be in a supraclavicular region on one of a left and right side of a sagittal plane of the patient, and the other depot of brown adipose tissue can be in a supraclavicular region on the other of the left and right side of the sagittal plane of the patient. The device can be removed and repositioned after the chemical has been delivered to the depot of brown adipose tissue for a threshold amount of time, e.g., at least seven days. The device can continuously deliver the chemical to the patient during the threshold amount of time. In response to a trigger event, the device can be removed from contact with tissue of the patient and repositioned to be in contact with another area of tissue of the patient proximate to another depot of brown adipose tissue. The trigger event can include at least one of the patient eating, the patient resting, a threshold temperature of the patient, a directional orientation of the patient, a change in the patient's weight, a change in the patient's tissue impedance, manual activation by the patient or other human, a blood chemistry change in the patient, and a signal from a controller in electronic communication with the device.

The device can have a variety of configurations. In one embodiment, the device can include a housing configured to be disposed in direct contact with the tissue of the patient proximate to the receptor in communication with at least a portion of the depot of brown adipose tissue, and a chemical source coupled to the housing and configured to deliver a chemical to the patient. The housing can include a housing of a patch attached to the patient. The chemical can be allowed to be delivered from the chemical source to the depot of brown adipose tissue during a first period of time, the chemical can be prevented from being delivered from the chemical source to the depot of brown adipose tissue during a second period of time after the first time period, and the chemical can be allowed to be delivered from the chemical source to the depot of brown adipose tissue during a third period of time after the second time period. In one embodiment, the device can include a controller configured to turn the chemical source on to start the delivery of the chemical to the patient, turn the chemical source off to stop the delivery of the chemical to the patient, or both. The controller can be configured to be located remotely from the patient and to be in electronic communication with the chemical source. The controller can be configured to be implanted entirely within the patient.

The chemical source can have a variety of configurations. In one embodiment, the chemical source can include a time-release pill. In another embodiment, the chemical source can be located within the housing. In yet another embodiment, the chemical source can include a reservoir contained within the housing and storing a supply of the chemical. The reservoir can be configured to deliver the chemical source to the depot of brown adipose tissue.

In another embodiment, a medical method is provided that includes positioning a device in contact with tissue of a patient proximate to a receptor in communication with at least a portion of a first depot of brown adipose tissue, activating the device to deliver a first chemical to the patient to activate the first depot and increase energy expenditure of the first depot, delivering the first chemical to the patient until a first threshold event occurs, when the first threshold event occurs, stopping delivery of the first chemical to the patient, delivering a second chemical to the patient to activate a receptor in communication with at least a portion of a second depot of brown adipose tissue and increase energy expenditure of the second depot, delivering the second chemical to the patient until a second threshold event occurs, and, when the second threshold event occurs, stopping delivery of the second chemical.

The first and second chemicals can have a variety of configurations. In one embodiment, the first and second chemicals are identical. In another embodiment, the first chemical can be configured to chemically interact with cellular surface receptors of the first depot. The second chemical can be configured to chemically interact with the cellular surface receptors of the first depot. The second chemical can include an activator configured to cause the first chemical to chemically interact with the cellular surface receptors of the first depot, and the first chemical can be inert until the first chemical is exposed to the second chemical.

The first and second chemical can be delivered to the patient in any number of ways. For example, at least one of the first and second chemicals can be delivered to the patient by injecting the at least one of the first and second chemicals into a circulatory system of the patient, thereby allowing the at least one of the first and second chemicals to circulate within the patient. Injecting the at least one of the first and second chemicals into the circulatory system of the patient can allow the at least one of the first and second chemicals to circulate within the patient to both of the first and second depots of brown adipose tissue.

In one embodiment, the first and second chemicals can be simultaneously delivered to the patient. In another embodiment, the first and second chemicals can be sequentially delivered to the patient such that the patient receives only one of the first and second chemicals at a time. When the second threshold event occurs, the device in contact with tissue of the patient proximate to the first depot can be activated to deliver the first chemical to the patient to activate the first depot and increase energy expenditure of the first depot.

The first threshold event can include, e.g., passage of a first predetermined amount of time, and the second threshold event can include, e.g., passage of a second predetermined amount of time. The first and second predetermined amounts of time can vary, such as each being at least about 24 hours or each being at least about seven days.

The first and second depots can have a variety of locations. In one embodiment, the first depot can be located on one of a left and right side of a sagittal plane of the patient, and the second depot can be located on the other of the left and right sides of the sagittal plane of the patient.

The method can have any number of variations. For example, the first chemical can be targeted to a nerve innervating the first depot of the brown adipose tissue to activate the first depot of brown adipose tissue. For another example, before delivering the second chemical to the patient, the device can be repositioned to be in contact with tissue of the patient proximate to the receptor in communication with at least a portion of the second depot, and the device can be used to deliver the second chemical to the patient. For yet another example, a second device can be positioned in contact with tissue of the patient proximate to the receptor in communication with at least a portion of the second depot, and the second device can be used to deliver the second chemical to the patient.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
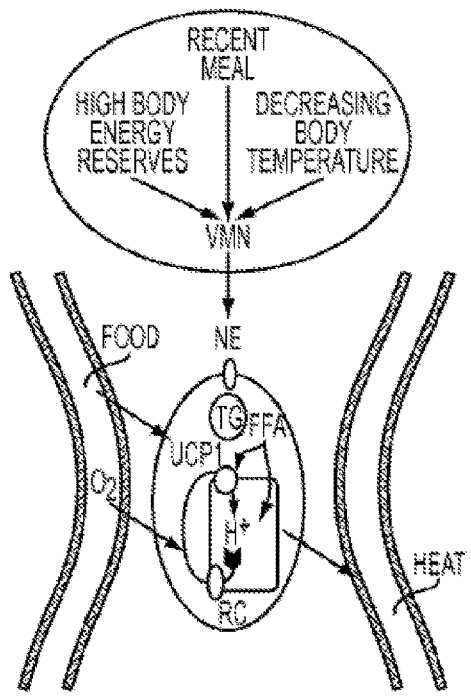
FIG. 1 is a schematic view of an oxidative phosphorylation cycle that occurs in mitochondria within BAT cells.
Figure 2:
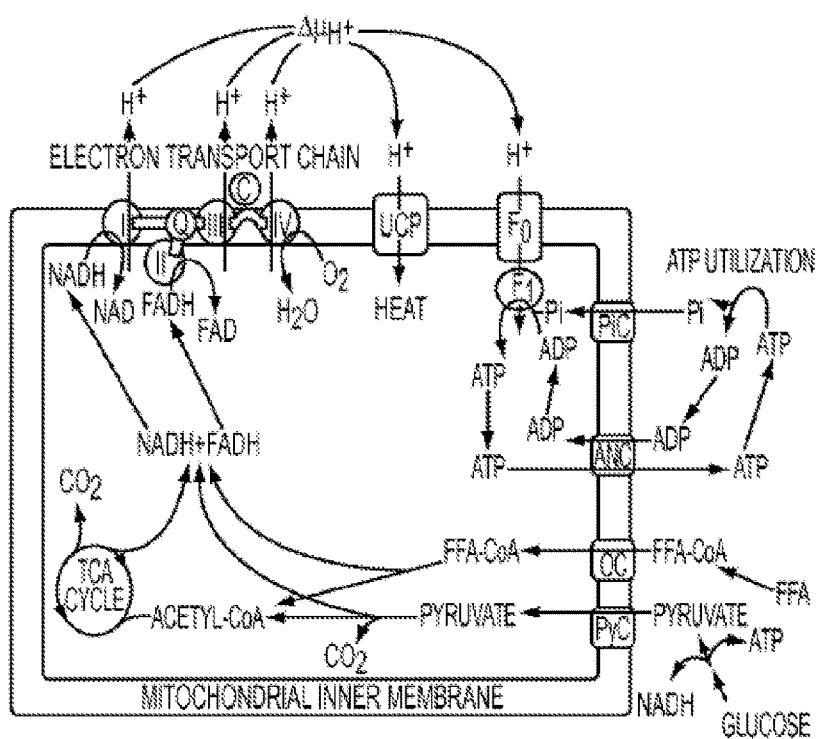
FIG. 2 is a schematic view of BAT mitochondria showing an oxidative phosphorylation cycle that occurs in the mitochondria.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for activating brown adipose tissue (BAT). In general, the methods and devices can activate BAT to increase thermogenesis, e.g., increase heat production and energy expenditure in the patient, which can treat metabolic disorders, such as obesity, diabetes, and hyperlipidemia. Therefore, activating BAT to increase thermogenesis can, over time, lead to one or more of weight loss, a change in the metabolism of the patient, e.g., increasing the patient's basal metabolic rate, and improvement of comorbidities in obese or non-obese patients, e.g., Type II diabetes, high blood pressure, etc. In an exemplary embodiment, a chemical configured to stimulate nerves that activate the BAT and/or to stimulate brown adipocytes directly can be delivered to a patient, thereby increasing thermogenesis in the BAT and inducing weight loss and/or improving metabolic function through energy expenditure. As will be appreciated by a person skilled in the art, an obese patient can have a body mass index (BMI) greater than 30 $kg/m^2$, and a non-obese patient can have a BMI less than 30 $kg/m^2$. In this way, weight loss and/or improved metabolic function can be induced without performing a major surgical procedure, without relying on cooling of the patient, and without surgically altering a patient's stomach and/or other digestive organs. A chemical, solution, drug, medicant, neutriceutical, or pharmaceutical administered to patient to activate BAT is generally referred to herein as a "chemical." As discussed further below, the chemical can be configured to elicit depolarization of a nerve pathway that ultimately results in activation of BAT. As also discussed further below, the chemical can be delivered to the patient locally and/or systemically to stimulate the nerves and/or the brown adipocytes. The chemical can be delivered locally to the patient by administering the chemical to a targeted area of the patient's body, such as directly to a BAT depot, to a region proximate to a BAT depot, or to a region containing receptors in communication with BAT that when activated results in the activation of BAT, such as by injecting the chemical directly into the targeted area or by positioning a chemical delivery device proximate to the targeted area. Alternatively or in addition, the chemical can be delivered systemically to the patient by introducing the chemical into a gastrointestinal tract, subcutaneous tissues, or a circulatory system of the patient. In this way, the chemical can be administered to the patient at any one or more selected body locations and can be allowed to circulate within the patient. In this way, regardless of where the chemical is delivered to a patient, e.g., at a shoulder area, orally, nasally, etc., the chemical can be circulated throughout the patient to reach and activate a plurality of BAT depots.

Following a surgical procedure to treat obesity such as Roux-en-Y gastric bypass (RYGB), a patient can lose weight due to an increase in energy expenditure, as demonstrated for example in a rodent model in Stylopoulos et al., "Roux-en-Y Gastric Bypass Enhances Energy Expenditure And Extends Lifespan In Diet-Induced Obese Rats," Obesity 17 (1 Oct. 2009), 1839-47. Additional data from Stylopoulos et al. (not published in the previous article or elsewhere as of the filing date of the present application) indicates that RYGB is also associated with increased levels of uncoupling protein 1 (UCP1), which is an uncoupling protein in mitochondria of BAT, as well as with a significant reduction in the size of fat stores within BAT and an increased volume of BAT. It thus appears that RYGB causes activation of BAT, although as discussed above, surgical procedures to treat obesity, such as gastric bypass, risk if not necessarily cause a variety of undesirable results. Devices and methods to activate BAT without a major surgical procedure like RYGB but instead by either endogenous or exogenous substance with stimulation to increase energy expenditure are therefore provided. One characteristic of BAT that distinguishes it from white adipose tissue (WAT) stores is the high number of mitochondria in a single BAT cell. This characteristic makes BAT an excellent resource for burning energy. Another distinguishing characteristic of BAT is that when activated, UCP1 is utilized to introduce inefficiency into the process of adenosine triphosphate (ATP) creation that results in heat generation. Upregulation of UCP1 is therefore a marker of BAT activation.

Activation of brown adipocytes leads to mobilization of fat stores within these cells themselves. It also increases transport of FFA into these cells from the extracellular space and bloodstream. FFAs in the blood are derived primarily from fats metabolized and released from adipocytes in WAT as well as from ingested fats. Stimulation of the sympathetic nervous system is a major means of physiologically activating BAT. Sympathetic nerve stimulation also induces lipolysis in WAT and release of EFA from WAT into the bloodstream to maintain FFA levels. In this way, sympathetic stimulation leads ultimately to the transfer of lipids from WAT to BAT followed by oxidation of these lipids as part of the heat generating capacity of BAT.

Figure 3:
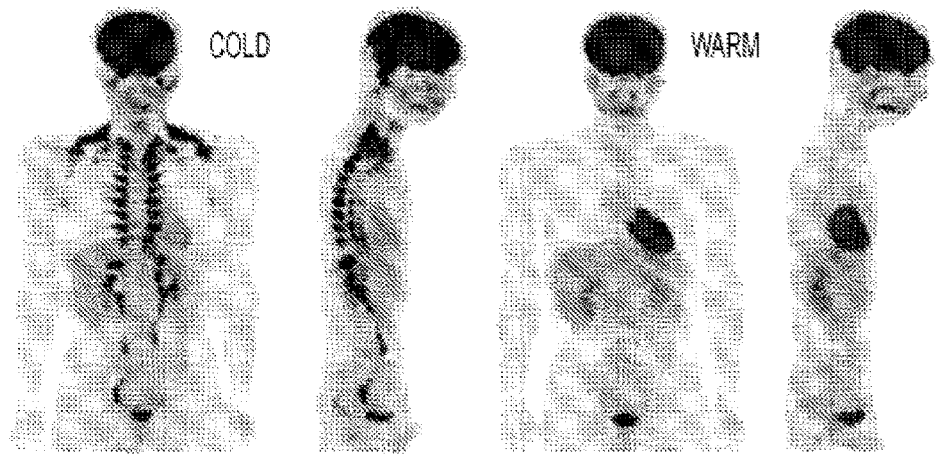
FIG. 3 is a schematic view of PET-CT images showing the locations of BAT depots in a patient subject to a cold environment and in the patient in a normal, warm environment.

The controlled activation of BAT can be optimized, leading to weight loss and/or improved metabolic function, by reducing the stores of triglycerides in WAT. A person skilled in the art will appreciate that exposure to cold temperature leads to the activation of BAT to help regulate body temperature. This knowledge allows the location of BAT to be readily assessed using positron emission tomography—computed tomography (PET-CT) imaging. FIG. 3 shows scans of a patient subjected to a cold environment (left two images) and the same patient scanned in a normal, warm environment (right two images). Shown in black are regions of intense glucose uptake—namely, the brain, the heart, the bladder, and in the cold environment, BAT. However these images show the locations of BAT depots—namely the nape of the neck, the supraclavicular region, over the scapula, alongside the spinal cord, and around the kidneys as referenced by, for example, Rothwell et al, "A Role For Brown Adipose Tissue In Diet-Induced Thermogenesis," Nature, Vol. 281, 6 Sep. 1979, and Virtanen et al., "Functional Brown Adipose Tissue in Healthy Adults," The New England Journal of Medicine, Vol. 360, No. 15, Apr. 9, 2009, 1518-1525. Applying cold to BAT and/or otherwise activating BAT as discussed herein can thus improve glucose tolerance in a patient, and thereby be effective to treat a metabolic disease such as diabetes independent of weight loss and regardless of whether the patient is obese or non-obese. For example, in their paper, Bartell et al., "Brown adipose tissue activity controls triglyceride clearance," Nature Medicine, Vol. 17, February 2011, 200-205, describe exposing mice to cold and detecting improved glucose tolerance after exposure to cold.

A person skilled in the art will appreciate that adult humans have substantial BAT depots, as indicated, for example, in J. M. Heaton, "The Distribution Of Brown Adipose Tissue In The Human," J Anat., 1972 May, 112(Pt 1): 35-39, and W. D. van Marken Lichtenbelt et al, "Cold-Activated Brown Adipose Tissue in Healthy Men," N. Engl. J. Med., 2009 April, 360, 1500-1508. A person skilled in the art will also appreciate that BAT is heavily innervated by the sympathetic nervous system, as indicated, for example, in Lever et al., "Demonstration Of A Catecholaminergic Innervation In Human Perirenal Brown Adipose Tissue At Various Ages In The Adult," Anat Rec., 1986 July, 215(3): 251-5, 227-9. Further, "[t]he thin unmyelinated fibers that contain norepinephrine (and not NPY) are those that actually innervate the brown adipocytes themselves. They form a dense network within the tissue, being in contact with each brown adipocyte (bouton-en-passant), and their release of norepinephrine acutely stimulates heat production and chronically leads to brown adipose tissue recruitment". B. Cannon, and J. Nedergaard, "Brown Adipose Tissue: Function And Physiological Significance," Physiol Rev., 2004: 84: 277-359.

Nerves innervating BAT can be stimulated to activate UCP1 and hence increase energy expenditure through heat dissipation through transcutaneous and/or direct stimulation of nerves innervating BAT. Transcutaneous and direct stimulation are each discussed below in more detail.

In some embodiments, transcutaneous and/or direct stimulation of nerves innervating BAT can be combined with one or more treatments, before and/or after transcutaneous and/or direct stimulation of BAT, which can help encourage BAT stimulation and/or increase an amount of BAT in a patient. For non-limiting example, a pharmaceutical can be administered to a patient, a light can be delivered to the patient, a magnetic field can be targeted to a region of the patient, the patient can be cooled, the patient can be heated, a BAT-stimulation procedure can be performed on the patient directed to a BAT depot and/or to a nerve innervating BAT, the patient can engage in weight loss therapies, and/or a surgical procedure can be performed on the patient, such as a procedure to induce weight loss and/or to improve metabolic function, e.g., glucose homeostatis, lipid metabolism, immune function, inflammation/anti-inflammatory balance, etc. A non-limiting example of cooling the patient includes applying a cold pack to skin of the patient for a period of time. The cold pack can be applied to a region of the skin with a high concentration of cold receptors, such as near the wrists, ankles, and/or regions having thermosensitive transient receptor potential (TRP) channels (e.g., TRPA1, TRPV1, TRPM8, etc.). Alternatively or in addition, the cold pack can be applied to the skin proximate to a BAT depot and/or to nerves innervating a BAT depot. Providing electrical stimulation, e.g., using an implanted electrical stimulation device, such that the BAT depot can be simultaneously activated through a mechanism associated with a lowered body temperature and electrically stimulated, thereby potentially further encouraging additive or synergistic activation of the BAT. Exemplary embodiments of methods and devices for delivering an electrical signal to activate BAT are described in more detail in U.S. Pat. Pub. No. 2011/0270360 filed Dec. 29, 2010 entitled "Methods And Devices For Activating Brown Adipose Tissue Using Electrical Energy." Non-limiting examples of a nerve stimulation technique configured to stimulate a nerve innervating BAT include delivery of a medium to the nerve that induces an action potential in the nerve, e.g., electricity, light, mechanical manipulation or vibration, a magnetic field, a chemical substance, etc. Non-limiting examples of a BAT-stimulation procedure include inducing differentiation of muscle, WAT, preadipocytes, or other cells to BAT, and/or implanting or transplanting BAT cells into a patient. Non-limiting examples of implanting or transplanting BAT cells include removing cells from a patient, culturing the removed cells, and reimplanting the cultured cells; transplanting cells from another patient; implanting cells grown from embryonic stem cells, adult stem cells, or other sources; and genetically, pharmacologically, or physically altering cells to improve cell function. Non-limiting examples of such weight loss therapies include a prescribed diet and prescribed exercise. Non-limiting examples of such a surgical procedure include gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, vagal nerve stimulation, duodenal endoluminal barrier, and procedures that allow for removal of food from the stomach. Combining one or more treatments, particularly a weight loss therapy or a weight loss surgical procedure which does not activate BAT, e.g., a procedure other than RYGB, biliopancreatic diversion (BPD) with or without duodenal switch, or some duodenal or other intestinal barrier (e.g., a prescribed diet and/or exercise program, adjustable gastric banding, vertical banded gastroplasty, sleeve gastrectomy, gastric plication, Magenstrasse and Mill, intragastric balloon therapy, some duodenal or other intestinal barrier, and small bowel transposition, with a means for acute or chronic activation of BAT such as the nerve stimulation discussed herein, can result in desirable patient outcomes through a combined approach.

Because BAT activation may lead to an increase in body temperature locally, regionally, or systemically, transcutaneous and/or direct stimulation of nerves innervating BAT can be combined with one or more heat dissipation treatments, before and/or after transcutaneous and/or direct stimulation of BAT. Non-limiting examples of such a heat dissipation treatment include inducing cutaneous/peripheral vasodilation, e.g., local or systemic administration of Alpha antagonists or blockers, direct thermal cooling, etc.

Figure 4:
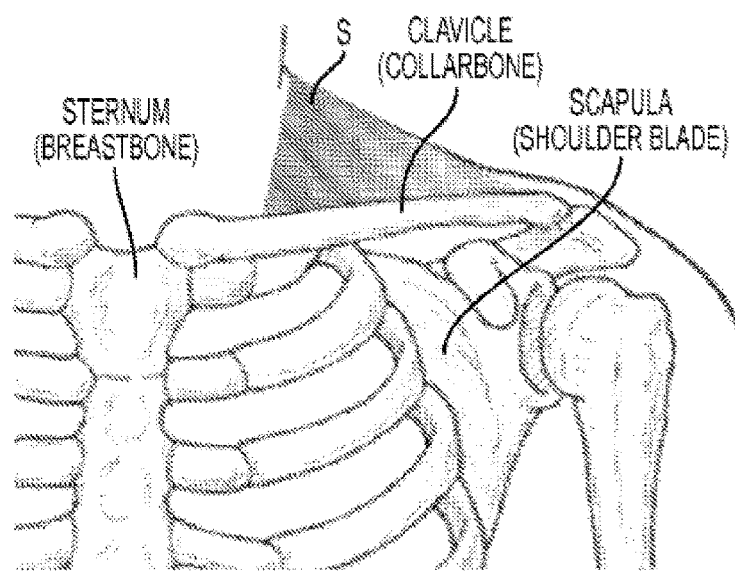
FIG. 4 is a transparent view of a portion of a human neck, chest, and shoulder area with a shaded supraclavicular region.

Whether BAT is activated directly and/or transcutaneously, target anatomical areas for BAT nerve stimulation and/or direct stimulation of brown adipocytes using a chemical can include areas proximate to BAT depots, e.g., a supraclavicular region, the nape of the neck, over the scapula, alongside the spinal cord, near proximal branches of the sympathetic nervous system that terminate in BAT depots, around at least one of the kidneys, the brain (e.g., molecules within the pathway such as activators of Melanocortin 4 and its associated ligands such as MSHα, etc.), and the gut (e.g., antagonists to CB-1 receptors, agonists of TRPV1, TRPA1, and TRPM8), and other receptors in the body that when stimulated result in the activation of BAT (e.g., cold receptors in the wrists and/or ankles, etc.). Any BAT depot can be selected for activation. For non-limiting example, in one embodiment illustrated in FIG. 4, a device (not shown) can be positioned proximate to an area over a scapula in a supraclavicular region S. Identification of one or more BAT depots for activation can be determined on an individualized patient basis by locating BAT depots in a patient by imaging or scanning the patient using PET-CT imaging, tomography, thermography, or any other technique, as will be appreciated by a person skilled in the art. Non-radioactive based imaging techniques can be used to measure changes in blood flow associated with the activation of BAT within a depot. In one embodiment, a contrast media containing microbes can be used to locate BAT. The contrast media can be injected into a patient whose BAT has been activated. An energy source such as low frequency ultrasound can be applied to the region of interest to cause destruction of bubbles from the contrast media. The rate of refill of this space can be quantified. Increased rates of refill can be associated with active BAT depots. In another embodiment, a contrast media containing a fluorescent media can be used to locate BAT. The contrast media can be injected into a patient whose BAT has been activated. A needle based probe can be placed in the region of interest that is capable of counting the amount of fluorescent contrast that passes the probe. Increased counts per unit time correspond to increased blood flow and can be associated with activated BAT depots. Because humans can have a relatively small amount of BAT and because it can be difficult to predict where BAT is most prevalent even near a typical BAT depot such as the nape of the neck, imaging a patient to more accurately pinpoint BAT depots can allow more nerves innervating BAT to be stimulated and with greater precision. Any number of BAT depots identified through patient imaging can be marked for future reference using a permanent or temporary marker. As will be appreciated by a person skilled in the art, any type of marker can be used to mark a BAT depot, e.g., ink applied on and/or below the epidermis, a dye injection, etc. The marker can be configured to only be visible under special lighting conditions such as an ultraviolet light, e.g., a black light.

Methods of measuring BAT activation can be determined through energy expenditure involving continuous measurements of heat output (direct calorimetry) or inhaled/exhaled gas exchange (indirect calorimetry) in subjects. The term "energy expenditure," as used herein, refers to the amount of energy (calories), that a person uses to breathe, circulate blood, digest food, support routine physiological functions and be physically active. To prevent weight gain, energy intake (caloric intake) must be balanced with energy expenditure.

Measurements of the heat released from a person's body can determine how much energy an activity has consumed. In addition, indirect calorimetry can measure oxygen consumption, carbon dioxide production and/or nitrogen excretion to calculate a ratio that reflects energy expenditure. A component of energy expenditure can be calculated as basal energy expenditure, which is the amount of energy required to maintain the body's normal metabolic activity, i.e. respiration, body temperature, etc.

Such energy expenditure or metabolic heat production in a subject can be assessed using several techniques. For measurement of the basal metabolic rate, the subject must be within its thermal neutral zone, which is the range of environmental temperatures across which the subject's body temperature can be maintained at its basal metabolic rate. The subject must be in a postabsorptive state, quiescent, in sexual repose, and resting but conscious. Since the latter prerequisite is often difficult to achieve with non-human subjects, the fasting heat production is used for animals which are quiet, but not necessarily resting.

Energy expenditure or metabolic heat production can be detected externally by a subject's heat loss pattern. Radiation, through which 40 to 60% of heat is lost from a subject, can be readily measured using any commercially available pyrometer or temperature sensor, since most radiated heat loss can be displayed in the 5-12 µm wavelength range of the electromagnetic spectrum. Direct and indirect calorimetry are further methods for assessing energy expenditure. Direct calorimetry measures heat loss from a subject directly by placing the subject at rest or exercising in a chamber surrounded by a waterjacket. Heat emitted from the subject raises the temperature of the water. The difference in the temperature of water entering and leaving the chamber reflects the subject's energy expenditure. Indirect calorimetry measures gas exchange and relates it to heat production. Indirect calorimetry involves monitoring of the amount of oxygen consumed (or conversely, the amount of carbon dioxide produced), and calculating the amount of energy expended by the subject, depending on the food substrate being utilized (e.g., fat, carbohydrate or protein).

Metabolic rate can also be measured through the use of doubly labeled water methods in which the average metabolic rate of an organism is measured over time. The use of doubly labeled water methods measures the subject's carbon dioxide production. Oxygen in body water can be lost in carbon dioxide, excretions and evaporative losses. However, hydrogen can only be lost through body water loss. Taking advantage of the change in body water and carbon dioxide production over time can be used to mathematically calculate metabolic rate.

Whether BAT is activated directly and/or transcutaneously, target cellular areas for BAT nerve stimulation and/or direct stimulation of brown adipocytes can include cell surface receptors (e.g., TGR5, $\beta_1AR$, $\beta_2AR$, $\beta_3AR$, etc.), nuclear receptors (e.g., PPAR$\gamma$, FXR, RXR, etc.), transcription co-activators and co-repressors (e.g., PGC1$\alpha$, etc.), intracellular molecules (e.g., 2-deiodinase, MAP kinase, etc.), UCP1 activators, individual cells and related components (e.g., cell surface, mitochondria, and organelles), transport proteins, PKA activity, perilipin and HSL (phospho PKA substrate), CREBP (cAMP response element-binding protein), adenosine monophosphate-activated protein kinase (AMPK), bile acid receptors (e.g., TGR5, FGF15, FXR, RXR $\alpha$, etc.), muscarinic receptors, etc.

In the course of treating a patient, BAT nerves and/or brown adipocytes can be stimulated at any one or more BAT depots directly or indirectly and can be stimulated simultaneously, e.g., two or more BAT depots being concurrently stimulated, or stimulated sequentially, e.g., different BAT depots being stimulated at different times. Simultaneous stimulation of BAT can help encourage more and/or faster energy expenditure. Sequential stimulation of BAT can help prevent the "burning out" of target nerves and can help stimulate the creation of new BAT cells. Sequential nerve stimulation can include stimulating the same BAT depot more than once, with at least one other BAT depot being activated before activating a previously activated BAT depot. Simultaneous and/or sequential stimulation can help prevent tachypylaxis.

The chemical, whether transcutaneously or directly delivered, can be configured in a variety of ways. A time between start of chemical deliveries for a chemical noncontinuously delivered to BAT can include can be of any regular, predictable duration, e.g., hourly, daily, coordinated around circadian, ultradian, or other cycles of interest, etc., such as about ten minutes, or can be of any irregular, unpredictable duration, e.g., in response to one or more predetermined trigger events, as discussed further below. Generally, the chemical can be configured to chemically interact with cellular surface receptors of BAT. In an exemplary embodiment, the chemical can include a depolarization agent, such as an activator of a channel causing depolarization, e.g., potassium, calcium, etc. In another exemplary embodiment, the chemical can include a hormone-related chemical, e.g., a thyroid hormone, Vitamin D, a bile acid, Retinol, etc. In still another exemplary embodiment, the chemical can include a Melanocortin receptor 4 (MCR4) protein agonist, TRPA1 agonists such as cinnamaldehyde and allyl isothiocyanate, TRPV1 agonists such as capsaicin and resiniferatoxin, and oleoylethanolamide (OEA). In another exemplary embodiment, the chemical can include an odiferous agent, e.g., eucalyptus, juniper, grapefruit, menthol, etc. Menthol can include a manufactured synthetic compound or can be obtained from one or more mint oils such as peppermint. One exemplary embodiment of menthol that can be delivered to a patient includes Bengay®, available from Johnson & Johnson of New Brunswick, N.J.

In still another exemplary embodiment, one chemical delivered to a patient can include an activator, and another chemical delivered to the patient can include an activatable effector (prodrug) configured to respond to the activator. Generally, the activator can be configured to activate the effector, which can be configured to be inert until the activator directly contacts, mixes with, or is otherwise applied to the effector. In other words, the effector can be configured to not appreciably bind with receptors in the patient until activated in a particular way, e.g., by coming into direct contact with the activator. The response of the effector to the activator can cause activation of BAT. Exemplary embodiments of an effector include beta adrenergic molecules configured to bind with G-protein coupled receptors on BAT without activating the receptors until an activator, e.g., a protease, is applied to the effector.

In an exemplary embodiment, the effector can be activated by altering its configuration, e.g., changing from an inert molecule to a molecule with a binding affinity for one or more receptors, so as to bind with receptors on a brown adipocyte that can activate BAT. Although the effector can be configured to be permanently changed, the effector can be configured to be deactivated with a second, different activator such that the molecule with a binding affinity changes back to the inert molecule. In other words, the effector can be configured to be activated by being exposed to a first activator, e.g., a chemical having a first composition, and to be deactivated by being exposed to a second chemical, e.g., a chemical having a second, different chemical composition. An effector configured to be permanently changed can allow for spatial specificity, e.g., for an effector to be delivered a particular target in the body, such as with a topically applied cream. An effector configured to be intermittently changed can allow for spatial and/or temporal specificity. In another embodiment, the effector can be activated by releasing molecules with a binding affinity for one or more receptors.

The effector and/or the activator can be systemically or locally delivered to a patient. Any adverse patient side effects of an effector and/or an activator can be reduced by locally delivering such an effector and/or activator such that the effector and/or activator are not circulated throughout the patient. In an exemplary embodiment, the effector can be systemically delivered to the patient, e.g., delivered through an injection or oral ingestion, such that the effector can circulate through a circulatory system of the patient. The activator can be locally delivered to the patient, e.g., targeted to a particular anatomical location having at least one BAT depot, such as a shoulder. In another exemplary embodiment, the activator can be systemically delivered to the patient, and the effector can be locally delivered to the patient.

The activator and the effector can be simultaneously or sequentially delivered to the patient. In an exemplary embodiment, the effector can be administered to a patient prior to delivery of the activator thereto such that when the activator is delivered to the patient, the activator can activate the previously administered effector. One effector can be administered to a patient such that only one effector is present in the patient's body, but any number of effectors can be simultaneously or sequentially administered to a patient such that a plurality of effectors are simultaneously present in the patient's body. If two or more effectors are administered to a patient, each of the effectors can be configured to respond to a different activator, e.g., to different chemical compositions, which can help avoid "burning out" of target areas, provide redundancy in case an activator or effector fails to be delivered, and allow a BAT depot to be continuously stimulated while helping to avoid burn-out from a particular chemical.

In one embodiment, the same chemical can be delivered to a particular BAT depot, either continuously or sequentially. In other words, a chemical can be continuously delivered to a particular BAT depot during a first period of time, delivery thereto can stop during a subsequent, second period of time, and then delivery thereto can begin again during a third period of time, etc. In another embodiment, a first chemical can be transcutaneously or directly delivered to a particular BAT depot, and then subsequently, either immediately thereafter or after a passage of a period of time, a second, different chemical can be delivered to the same particular BAT depot. In this way, chances of a BAT depot adapting to a particular stimulus, e.g., to a specific cell surface receptor agonist, can be reduced, thereby helping to prevent the BAT depot from becoming less receptive to chemical stimulation.

The chemical can be administered to a patient in any number of ways, as will be appreciated by a person skilled in the art. In one embodiment, a chemical can be administered to a patient by injecting the chemical into the patient, e.g., using a needle. The chemical can be injected at any one or more locations, e.g., directly into a BAT depot, into a patient's circulatory system, subcutaneous tissue, etc. A particular depth of a needle can be selected to help ensure that the chemical is injected into a desired target. By injecting the chemical into a circulatory system of the patient, the chemical can be administered to the patient at any one or more selected body locations and can be allowed to circulate within the patient.

In another embodiment, a chemical can be administered to a patient by topically applying the chemical to an exterior surface of a patient's skin, such as by applying a gel or cream thereto. The chemical can be topically applied at any location on a patient's body that would result in activation of BAT, but in an exemplary embodiment, the chemical can be topically applied at a skin surface proximate to a BAT depot. In another exemplary embodiment, the chemical can include a TRP agonist configured to target receptors in skin such as TRPV1, TRPA1, TRPM8, and the like. Similar to that discussed above regarding an injected chemical, a topically applied chemical can be configured to circulate within the patient.

In still another embodiment, a chemical can be administered to a patient by administering a pill containing the chemical to the patient. The pill can be administered to the patient in any way, e.g., swallowing, as will be appreciated by a person skilled in the art. In an exemplary embodiment, the pill can be delivered to a patient's gut, e.g., stomach and/or intestine, which can target antagonists to CB-1 receptors that reside within the gut, affecting the enzyme that metabolizes endogenous cannabinoids (fatty acid amide hydrolase), agonists of TRPV1, TRPA1, and TRPM8, and that lead to activation of BAT. Various exemplary embodiments of controlling drug delivery to a targeted region of the body using a pill are described in more detail in U.S. patent application Ser. No. 12/976,648 filed Dec. 22, 2010 entitled "Pill Catchers" and in U.S. Pat. Pub. No. 2009/0018594 filed Oct. 4, 2007 entitled "Methods And Devices For Medical Treatment."

In yet another embodiment, a chemical can be administered to a patient through inhalation, e.g., using a nasal spray.

A chemical can be delivered to a patient continuously or intermittently. In an exemplary embodiment, a chemical can be intermittently delivered to a patient by alternating at least once between delivering the chemical to the patient during a first period of time and not delivering the chemical to the patient during a second period of time.

In an exemplary embodiment, a chemical can be continuously delivered to a patient through time-release administration, e.g., via a pill, microsphere, patch, etc., to the patient. The time-release pill or microsphere can be configured to constantly release relatively small doses of a chemical into the patient. The chemical can be released on any time schedule, e.g., a particular chemical dosage or volume released for one hour every two hours for a total of four one-hour releases. In an exemplary embodiment, an amount of menthol, e.g., Bengay® ointment can be topically applied to a patient's skin for a period of time, e.g., one hour. Various methods of applying menthol are described in further detail in Tajino K, et al, "Application Of Menthol To The Skin Of Whole Trunk In Mice Induces Autonomic And Behavioral Heat-Gain Responses," Am J Physiol Regul Integr Comp Physiol. 2007 November; 293(5):R2128-35, Epub 2007 Aug. 29. One embodiment of a time-release patch includes a 3M CoTran™ Membrane available from 3M of St. Paul, Minn.

Another exemplary embodiment of an intermittent delivery includes a chemical time-released, e.g., via a pill, microsphere, patch, etc., such that it can be alternately released during a first period of time and not be released during a second period of time.

Another exemplary embodiment of an intermittent delivery includes a pump, e.g., an infusion pump, configured to sporadically release a chemical contained in a reservoir. The chemical can be released on a regular schedule, e.g., released for ten seconds every ten minutes, or on an irregular schedule, e.g., in response to a predetermined trigger event or whenever the pump is manually activated. The reservoir can be refillable and/or replaceable. In one embodiment, the reservoir can be refillable by removing reservoir from the patient, adding an amount of chemical to the reservoir, and reattaching or reimplanting the reservoir. In another embodiment, the reservoir can be configured to be refillable when implanted within a patient, such as by using a needle inserted through the patient's skin, through a needle-penetrable, self-sealing septum extending across the reservoir, and into the reservoir, as will be appreciated by a person skilled in the art. The pump and/or the reservoir in communication therewith can be implanted or transdermal. In one embodiment, a reservoir storing a supply of a chemical, e.g., a liquid drug, can be contained within a housing. The housing can be configured to be implanted within a patient or to be located external to a patient, such as by being applied to an external skin surface of the patient such as with an adhesively-attached patch. Whether implanted within a patient or not, the reservoir can have an elongate delivery tube such as a catheter coupled thereto such that the chemical contained with the reservoir can be released into the catheter and flow through the catheter to a location remote from the reservoir. Various exemplary embodiments of transcutaneous and/or implantable pumps and reservoirs configured to deliver a fluid to a patient are described in more detail in U.S. Pat. No. 4,978,338 filed Jun. 20, 1988 entitled "Insulin Infusion Pump," U.S. Pat. No. 4,498,843 filed Aug. 2, 1982 entitled "Implantable Infusion Apparatus," U.S. Pat. Pub. No. 2009/0204131 filed Feb. 12, 2008 entitled "Automatically Adjusting Band System With MEMS Pump," U.S. Pat. Pub. No. 2009/0171375 filed Dec. 27, 2007 entitled "Controlling Pressure In Adjustable Restriction Devices."

Another exemplary embodiment of an intermittent chemical delivery includes periodic injections of a chemical into a patient. The injections can occur on a regular schedule, e.g., once every week, or irregularly, e.g., when a predetermined trigger event such as eating occurs.

A chemical delivered to a BAT depot can be delivered continuously, in predetermined intervals, in sporadic or random intervals, in response to one or more predetermined trigger events, or in any combination thereof. If the chemical is continuously delivered to the patient, particular care should be taken to ensure that the chemical delivered to the patient will not damage the target nerves or tissues. For a chemical delivered intermittently, nerve or tissue damage can be reduced, if not entirely prevented, by selecting an on/off ratio in which the chemical is not delivered, e.g., "off," for more time than it is delivered, e.g., "on." For non-limiting example, a chemical can be delivered to BAT intermittently with an on/off ratio of about 1:19, e.g., a chemical delivered for 30 seconds every ten minutes (30 seconds on/9.5 minutes off). The device delivering the chemical can be configured to respond to one or more predetermined trigger events, e.g., events that are sensed by or otherwise signaled to the device. Non-limiting examples of trigger events include the patient eating, the patient resting (e.g., sleeping), a threshold temperature of the patient (e.g., a temperature in the stimulated BAT depot or a core temperature), a directional orientation of the patient (e.g., recumbent as common when sleeping), a change in the patient's weight, a change in the patient's tissue impedance, manual activation by the patient or other human (e.g., via an onboard controller, via a wired or wirelessly connected controller, or upon skin contact), a blood chemistry change in the patient (e.g., a hormonal change), low energy expenditure, menstrual cycles in women, medication intake (e.g., an appetite suppressant such as topiramate, fenfluramine, etc.), a nutrient change in the patient (e.g., a change in glucose or glucose transporters, amino acids, bile acids, free fatty acids and fatty acid transporters, and their metabolites, etc.), and a manually-generated or automatically-generated signal from a controller in electronic communication, wired and/or wireless, with the device. Non-limiting examples of nutrients include lipids such as bile acids, cholesterol and its metabolites, aliphatic fatty acids, peptides and proteins, etc. The controller can be internal to the device, be located external from but locally to device, or be located external and remotely from device. As will be appreciated by a person skilled in the art, the controller can be coupled to the device in any way, e.g., hard-wired thereto, in wireless electronic communication therewith, etc. In some embodiments, multiple devices can be applied a patient, and at least two of those devices can be configured to deliver a chemical based on different individual trigger events or combinations of trigger events.

Figure 5:
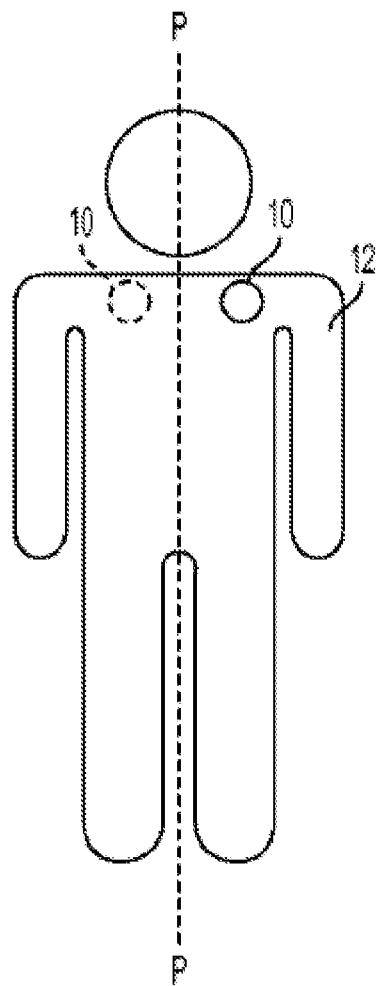
FIG. 5 is a front view of a body showing one embodiment of an electrical stimulation device positioned on opposite sides of the body's sagittal plane.

Generally, transcutaneous stimulation of BAT can include applying a device to an exterior skin surface of a patient proximate to a BAT depot and activating the device to deliver a chemical to the BAT depot. In this way, the chemical can activate the BAT proximate to the device by stimulating the nerves innervating the BAT and/or by stimulating brown adipocytes directly. As mentioned above, two or more transcutaneous devices, same or different from one another, can be simultaneously applied to a patient, proximate to the same BAT depot or to different BAT depots. Although a patient can have two or more transcutaneously applied devices and although the devices can be configured to simultaneously deliver a chemical to BAT, the devices can be configured such that only one delivers a chemical at a time. As also mentioned above, a transcutaneous device can be rotated to different BAT depots of a patient and deliver a chemical to each of the BAT depots. Rotating a device between two or more different locations on a patient's body and/or removing a device from a patient when not in use can help prevent nerve or tissue desensitization and/or dysfunction, can help reduce any adverse effects of a device's attachment to the body, e.g., irritation from an adhesive applying a device to skin, and/or can help stimulate creation or replication of new BAT in multiple locations on a patient's body. For non-limiting example, the device can be placed in varying positions on the body to modulate the activity of different regions of BAT. In one embodiment, the device can be worn on one side of the neck, e.g., the left side, for a period of time and then on an opposite side of the neck, e.g., the right side, for the next time period, etc. In another embodiment, the device can be worn on an anterior side of a BAT depot, e.g., front of a left shoulder on one side of the patient's coronal plane, for a period of time and then on an opposite, posterior side of the BAT depot, e.g., back of the left shoulder on the opposite side of the patient's coronal plane, for the next period of time. In yet another embodiment, illustrated in FIG. 5, a device 10 can be worn proximate to a BAT depot on one of a left and right side of a sagittal plane P in a supraclavicular region of a body 12 for a period of time and then the device 10 can be worn on the other of the left and right sides of the sagittal plane P in the supraclavicular region proximate to another BAT depot for the next period of time. Although the same device 10 is shown in FIG. 5 as being sequentially relocated to different tissue surface or skin positions on the body 12, as discussed herein, one or both of the devices can be implanted and/or two separate devices can be used with a patient such that a first device is positioned at one location and a second device is positioned at a second, different location.

The transcutaneous device used to transcutaneously activate BAT can have a variety of sizes, shapes, and configurations. Generally, the device can be configured to deliver a chemical to tissue at predetermined intervals, in response to a manual trigger by the patient or other human, in response to a predetermined trigger event, or any combination thereof. A transcutaneous device configured to deliver a chemical, such as a transdermal patch, can have a shape configured to conform to a patient's anatomy, e.g., to fit around a patient's neck and over the patient's clavicles, to help minimize, if not eliminate, slippage or unsticking of the patch from the patient's skin. In an exemplary embodiment, a transcutaneous device can be attached to a patient during sleep, although a transcutaneous device can be applied to a patient at any time. Various exemplary embodiment of devices configured to transdermally deliver a chemical are described in more detail in U.S. Pat. No. 6,532,386 filed Aug. 30, 1999 entitled "Electrotransort Device Comprising Blades," U.S. Pat. No. 6,072,100 filed Jan. 28, 1998 entitled "Extrudable Compositions For Topical Or Transdermal Drug Delivery," and U.S. Pat. No. 7,300,409 filed Oct. 17, 2005 entitled "Therapy Patch."

Optionally, a patch or other transdermal device can be attached to a patient using a placement tool. Generally, the placement tool can facilitate consistent placement of the device on the patient's skin proximate to a targeted area, e.g., a BAT depot. In one embodiment, the placement tool can be aligned with a bony landmark of the patient, e.g., connecting medial and lateral heads of clavicle and/or acromion of the scapula, such that after alignment thereto, the targeted area can be repeatedly consistently identified via the placement tool. Bony landmarks can be identified in any way, such as by imaging the patient prior to application of the device, as discussed above. The placement tool can be a standalone instrument, or it can be built into the device, e.g., the device and/or adhesive attaching the device to the patient including one or more grid marks, numbers, letters, or other measurement markings.

Various exemplary embodiments of transcutaneous devices configured to stimulate nerves are described in more detail in U.S. Patent Publication No. 2009/0132018 filed Nov. 16, 2007 and entitled "Nerve Stimulation Patches And Methods For Stimulating Selected Nerves," U.S. Patent Publication No. 2008/0147146 filed Dec. 19, 2006 and entitled "Electrode Patch And Method For Neurostimulation," U.S. Patent Publication No. 2005/0277998 filed Jun. 7, 2005 and entitled "System And Method For Nerve Stimulation," U.S. Patent Publication No. 2006/0195153 filed Jan. 31, 2006 and entitled "System And Method For Selectively Stimulating Different Body Parts," U.S. Patent Publication No. 2007/0185541 filed Aug. 2, 2006 and entitled "Conductive Mesh For Neurostimulation," U.S. Patent Publication No. 2006/0195146 filed Jan. 31, 2006 and entitled "System And Method For Selectively Stimulating Different Body Parts," U.S. Patent Publication No. 2008/0132962 filed Dec. 1, 2006 and entitled "System And Method For Affecting Gastric Functions," U.S. Patent Publication No. 2008/0147146 filed Dec. 19, 2006 and entitled "Electrode Patch And Method For Neurostimulation," U.S. Patent Publication No. 2009/0157149 filed Dec. 14, 2007 and entitled "Dermatome Stimulation Devices And Methods," U.S. Patent Publication No. 2009/0149918 filed Dec. 6, 2007 and entitled "Implantable Antenna," U.S. Patent Publication No. 2009/0132018 filed Nov. 16, 2007 and entitled "Nerve Stimulation Patches And Methods For Stimulating Selected Nerves," U.S. patent application Ser. No. 12/317,193 filed Dec. 19, 2008 and entitled "Optimizing The Stimulus Current In A Surface Based Stimulation Device," U.S. patent application Ser. No. 12/317,194 filed Dec. 19, 2008 and entitled "Optimizing Stimulation Therapy Of An External Stimulating Device Based On Firing Of Action Potential In Target Nerve," U.S. patent application Ser. No. 12/407,840 filed Mar. 20, 2009 and entitled "Self-Locating, Multiple Application, And Multiple Location Medical Patch Systems And Methods Therefor," U.S. patent application Ser. No. 12/605,409 filed Oct. 26, 2009 and entitled "Offset Electrodes."

In an exemplary embodiment, the transcutaneous device can include a chemical stimulation patch configured to be applied to an external skin surface and to deliver a chemical to tissue below the skin surface, e.g., to underlying BAT. The chemical can be delivered any depth below the skin surface, such as up to about 2 cm below the skin surface, e.g., at a maximum penetration depth in a range of about 1 to 2 cm. The patch can be configured to deliver a chemical from an on-board chemical source and/or to deliver a chemical received by the patch from a chemical source in communication with the patch, e.g., through a delivery tube such as a catheter extending between the patch and the chemical source. The device can be wireless and be powered by an on-board and/or external source, e.g., inductive power transmission. The patch can be attached to the skin in any way, as will be appreciated by a person skilled in the art. Non-limiting examples of patch application include using a skin adhesive locally (e.g., on patch rim), using a skin adhesive globally (e.g., on skin-contacting surfaces of the patch), using an overlying support (e.g., gauze with taped edges), using an adherent frame allowing interchangeability (e.g., a brace or an article of clothing), being subdermally placed with wireless connectivity (e.g., Bluetooth), and using any combination thereof. The device can include receiver circuitry configured to interact with a controller in electronic communication with a chemical source, e.g., a reservoir or supply, of the device such that the controller can control at least some functions of the chemical release mechanism, e.g., on/off status of the chemical and adjustment of parameters such as release timing and volume of chemical released, etc. In an exemplary embodiment, a chemical stimulation patch can include a plurality of reservoirs, each of which can be the same as or different from any one or more of the other reservoirs. The reservoirs can each be configured to contain a different chemical configured to be delivered to the patient.

In use, and as mentioned above, a chemical stimulation patch can be worn continuously or intermittently as needed. The patch can be placed proximate to a BAT depot, such as over the left supraclavicular region of the patient's back, for a predetermined amount of time, e.g., twelve hours, one day, less than one week, seven days (one week), one month (four weeks), etc., and can continuously deliver a chemical to the BAT. As mentioned above, the BAT depot can be identified by imaging the patient prior to application of the patch proximate to the BAT depot. Seven days is likely the longest period an adhesive can be made to stick to the skin of a patient without modification and can thus be a preferable predetermined amount of time for patches applied to skin with an adhesive. After the predetermined amount of time, the patch can be removed by a medical professional or the patient, and the same patch, or more preferably a new patch, can be placed, e.g., on the right supraclavicular region of the patient's back for another predetermined amount of time, which can be the same as or different from the predetermined amount of time as the first patch applied to the patient. This process can be repeated for the duration of the treatment, which can be days, weeks, months, or years. In some embodiments, the process can be repeated until occurrence of at least one threshold event, e.g., a predetermined amount of time, a predetermined physiological effect such as a predetermined amount of weight lost by the patient, etc. If the same patch is relocated from a first region, e.g., the left supraclavicular region, to a second region, right supraclavicular region, the patch can be reconditioned after removal from the first region and prior to placement at the second region. Reconditioning can include any one or more actions, as will be appreciated by a person skilled in the art, such as replacing one or more patch components, e.g., a battery, an adhesive, etc.; cleaning the patch; etc.

In one embodiment of intermittent chemical delivery using pump, a patient can wear an infusion style pump storing a supply of a chemical configured to target a cellular surface of a BAT depot, e.g., a beta adrenergic receptor agonist such as norepinephrine. A delivery mechanism, e.g., a needle, can be coupled to the pump to directly deliver the chemical into a vicinity of the BAT depot. The pump can be configured to start pumping a predetermined clinically relevant amount of the chemical through the needle upon occurrence of a predetermined trigger event, e.g., when the patient begins eating a meal. In one embodiment, the patient eating can be determined through a detection of heart rate variability, as discussed in more detail in U.S. patent application Ser. No. 12/980,695 filed Dec. 29, 2010 and entitled "Obesity Therapy And Heart Rate Variability" and U.S. patent application Ser. No. 12/980,710 filed Dec. 29, 2010 and entitled "Obesity Therapy And Heart Rate Variability." The pump can be configured to quickly ramp up and then slowly ramp down delivery of the chemical over a predetermined period of time, e.g., thirty minutes. Such intermittent chemical delivery can be particularly effective if the patient previously underwent a surgical procedure to treat obesity that does not activate energy expenditure, such as a laparoscopic adjustable gastric banding procedure.

In another embodiment of intermittent chemical delivery using a pump, a patient can wear an infusion style pump storing a supply of a chemical configured to target bile acid receptors, e.g., agonists configured to bind with TGR5 receptors on BAT. A delivery mechanism can be coupled to the pump to deliver the chemical into a circulatory system of the patient, similar to delivery of insulin to a diabetic patient, as will be appreciated by a person skilled in the art. The pump can be configured to start pumping a predetermined clinically relevant amount of the chemical at a prescribed, constant rate through the needle upon occurrence of a first predetermined trigger event, e.g., when the patient begins eating a meal. In one embodiment, the patient eating can be detected by a glucose monitor, such as by using one or more readings measured by the glucose monitor to determine satisfaction of a pre-programmed algorithm, e.g., when the patient's glucose level exceeds a predetermined threshold value or when the patient's glucose level increases or decreases a predetermined amount over a predetermined period of time. The chemical can be continuously delivered to the patient until occurrence of a second predetermined trigger event, such as passage of a predetermined amount of time, at which time the pump can stop pumping the chemical to the patient. The first and second trigger events can be the same as or different from each other. Such intermittent chemical delivery can be particularly effective as standalone therapy.

In one embodiment of continuous chemical delivery using pump, a patient can wear an infusion style pump storing a supply of an MC4 receptor agonist configured to target sympathetic nerves ultimately innervating BAT. A delivery mechanism, e.g., a needle, can be coupled to the pump to directly deliver the chemical into a vicinity of the sympathetic nerves innervating BAT. Patient side effects of the chemical can be reduced by releasing the chemical into the patient at a site with receptors for the chemical and at a site along the sympathetic chain innervating the BAT depot of interest that is as close as possible to the BAT depot. The pump can be configured to continuously pump a predetermined clinically relevant amount of the chemical through the needle to maintain a substantially consistent level of BAT activation when the patient is at rest. The pump can start continuously pumping when a first predetermined trigger event occurs, e.g., the pump wirelessly receiving an electronic start signal or the pump being manually button or switch activated by the patient. Upon occurrence of a second predetermined trigger event, e.g., when the patient begins eating a meal, the pump can be configured to increase an amount of chemical being delivered to the patient. The increased amount can be continuously delivered to the patient until occurrence of a third predetermined trigger event, such as passage of a predetermined amount of time, at which time the pump can resume pumping the previous predetermined clinically relevant amount of the chemical to the patient. Any of the first, second, and third trigger events can be the same as or different from any of the other trigger events. Such continuous chemical delivery can be particularly effective if the patient is on a medically prescribed diet and exercise program.

To more accurately simulate a weight loss surgery and/or invasive metabolic disorder treatment that has a continuous or chronic effect on a patient for an extended period of time, the patch can be placed on a patient and continuously or chronically deliver a chemical thereto for an extended, and preferably predetermined, amount of time. In an exemplary embodiment, the predetermined amount of time can be at least four weeks. The chemical can be delivered to same BAT depot for the predetermined amount of time, or two or more different BAT depots can be stimulated throughout the predetermined amount of time, e.g., left and right supraclavicular regions being stimulated for alternate periods of seven days to total one month of predetermined time. Continued or chronic nerve stimulation to activate BAT can increase BAT energy expenditure over time and potentially induce more or faster weight loss and/or metabolism change than periodic or intermittent nerve stimulation. The chemical can be the same or can vary during the amount of time such that the chemical is continuously and chronically applied to the patient to provide 24/7 treatment mimicking the 24/7 consequences of surgery. The chemical can vary by e.g., by being delivered at different volumes or dosages, by first delivering a first chemical and then delivering a second, different chemical, etc. The continuous amount of time the patient is stimulated with a chemical can be a total amount of continuous activation of any one BAT depot (e.g., activation of a single BAT depot), sequential activation of two or more BAT depots, simultaneous activation of two or more BAT depots, or any combination thereof. A total amount of time of sequential activation of different BAT depots can be considered as one extended amount of time despite different areas of BAT activation because activation of one BAT depot may cause the brain to signal for BAT activation in other BAT depots.

Generally, direct activation of BAT can include implanting a device below the skin surface proximate to a BAT depot, e.g., within a BAT depot, and activating the device to deliver a chemical to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art. The device can be implanted on a nerve or placed at or near a nerve cell's body or perikaryon, dendrites, telodendria, synapse, on myelin shelth, node of Ranvier, nucleus of Schwann, or other glial cell to stimulate the nerve. While implanting such a device can require a surgical procedure, such implantation is typically relatively short, outpatient, and with greatly reduced risks from longer and more complicated surgical procedures such as gastric bypass. In an exemplary embodiment, a stimulation device with at least one chemical source can be at least partially implanted in the patient, and more preferably entirely within the patient. A person skilled in the art will appreciate that any number of chemical sources, e.g., one or more each delivering a chemical same or different from any of the other chemical sources, can be at least partially implanted in the patient. The chemical source can be implanted in a location sufficiently close to the nerves innervating the BAT so that when activated, the chemical released from the chemical source is sufficiently transferred to adjacent nerves, causing these nerves to depolarize. As mentioned above, the device can include receiver circuitry configured to interact with a controller in electronic communication with the chemical source such that the controller can control at least some functions of the chemical source, e.g., on/off status of the light source, switching between multiple chemical sources included in the device, and adjustment of parameters such as dosage, etc.

Various exemplary embodiments of devices configured to directly apply a signal to stimulate nerves are described in more detail in U.S. Patent Publication No. 2005/0177067 filed Jan. 26, 2005 and entitled "System And Method For Urodynamic Evaluation Utilizing Micro-Electronic Mechanical System," U.S. Patent Publication No. 2008/0139875 filed Dec. 7, 2006 and entitled "System And Method For Urodynamic Evaluation Utilizing Micro Electro-Mechanical System Technology," U.S. Patent Publication No. 2009/0093858 filed Oct. 3, 2007 and entitled "Implantable Pulse Generators And Methods For Selective Nerve Stimulation," U.S. Patent Publication No. 2010/0249677 filed Mar. 26, 2010 and entitled "Piezoelectric Stimulation Device," U.S. Patent Publication No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Patent Publication No. 377695 published as International Patent Publication No. WO1989011701 published Nov. 30, 2004 and entitled "Interrogation And Remote Control Device."

In use, at least one chemical source of an implantable stimulation device can be placed in the area of a BAT depot. The chemical source can be in electronic communication with a device external to the patient's skin to adjust characteristics such as release volume, release timing, etc. The external device can be positioned near the patient's skin, e.g., using a belt, a necklace, a shirt or other clothing item, furniture or furnishings such as a chair or a pillow, or can be a distance away from the patient's skin, such as a source located elsewhere in the same room or the same building as the patient. The chemical stimulation device can include circuitry configured to control an activation distance, e.g., how close to a power source the chemical stimulation device must be to be powered on and/or begin delivering a chemical to the patient. Correspondingly, the external device can include a transmitter configured to transmit a signal to the chemical stimulation device's circuitry. If implanted, the device can include an internal power source, e.g., a battery, a capacitor, stimulating electrodes, a kinetic energy source such as magnets positioned within wired coils configured to generate energy within the coils when shaken or otherwise moved, etc. In one embodiment, a battery can include a flexible battery, such as a Flexion battery available from Solicore, Inc. of Lakeland, Fla. In another embodiment, a battery can include an injectable nanomaterial battery. The power source can be configured to be recharged by transcutaneous means, e.g., through transcutaneous energy transfer (TET) or inductive coupling coil, and/or can be configured to provide power for an extended period of time, e.g., months or years, regardless of how long the power source is intended to provide power to the device. In some embodiments, a power source can be configured to provide power for less than an extended period of time, e.g., about 7 days, such as if a battery is replaceable or rechargeable and/or if device real estate can be conserved using a smaller, lower power battery.

The controller, and/or any other portion of the device or external device, as will be appreciated by a person skilled in the art, can be configured to measure and record one or more physical signals relating to the activation of BAT. For non-limiting example, the physical signals can include voltage, current, impedance, temperature, time, moisture, salinity, pH, concentration of hormones or other chemicals, etc. The recorded physical signals can be presented to the patient's physician for evaluation of system performance and efficacy of brown adipose activation. Also, the recorded physical signals can be used in a closed-loop feedback configuration to allow the device, e.g., the controller, to dynamically adjust the chemical settings used for treatment.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Patent Publication No. 2009/0202387 filed Feb. 8, 2008 and entitled "System And Method Of Sterilizing An Implantable Medical Device."

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical device, comprising:
a pump configured to be applied to an exterior skin surface of a patient at a depot of brown adipose tissue and in communication with a receptor in communication with at least a portion of the depot of brown adipose tissue,
wherein the pump has an on-board supply of a chemical, and the pump applied to the exterior skin surface delivers the chemical to the patient to activate the brown adipose tissue and increase energy expenditure of the brown adipose tissue, wherein the delivered chemical is configured to chemically interact with cellular surface receptors of the brown adipose tissue, and the chemical comprises one of a depolarization agent, a hormone-related chemical, an odiferous agent, a Melanocortin receptor 4 (MCR4) protein agonist, a TRPA1 agonist, and a TRPV1 agonist.

2. The device of claim 1, wherein the pump has a reservoir containing the on-board supply of the chemical.

3. The device of claim 1, wherein the pump has an on-board controller configured to control the delivery of the chemical based on a predetermined delivery plan.

4. The device of claim 3, wherein the predetermined delivery plan includes continuous release of the chemical from the pump for a predetermined amount of time.

5. The device of claim 4, wherein the predetermined amount of time is in a range of twelve hours to four weeks.

6. The device of claim 3, wherein the predetermined delivery plan includes the controller causing a start of the delivery of the chemical in response to a trigger event, wherein the trigger event includes at least one of the patient eating, the patient resting, a threshold temperature of the patient, a directional orientation of the patient, a change in the patient's weight, a change in the patient's tissue impedance, manual activation by the patient or other human, and a blood chemistry change in the patient.

7. A medical device, comprising:
a patch configured to be applied to an exterior skin surface of a patient at a depot of brown adipose tissue and in communication with a receptor in communication with at least a portion of the depot of brown adipose tissue,
wherein the patch applied to the exterior skin surface delivers a chemical to the patient to activate the brown adipose tissue and increase energy expenditure of the brown adipose tissue, wherein the delivered chemical is configured to chemically interact with cellular surface receptors of the brown adipose tissue, and the chemical comprises one of a depolarization agent, a hormone-related chemical, an odiferous agent, a Melanocortin receptor 4 (MCR4) protein agonist, a TRPA1 agonist, and a TRPV1 agonist and wherein the patch has an on-board supply of the chemical that is delivered to the patient or the chemical is received by the patch from a chemical source in communication with the patch that is delivered to the patient.

8. The device of claim 7, wherein the patch has a reservoir containing the on-board supply of the chemical.

9. The device of claim 7, wherein the patch has an on-board controller configured to control the delivery of the chemical based on a predetermined delivery plan.

10. The device of claim 9, wherein the predetermined delivery plan includes continuous release of the chemical from the patch for a predetermined amount of time.

11. The device of claim 10, wherein the predetermined amount of time is in a range of twelve hours to four weeks.

12. The device of claim 10, wherein the predetermined amount of time is seven days or less.

13. The device of claim 9, wherein the predetermined delivery plan includes the controller causing a start of the delivery of the chemical in response to a trigger event, wherein the trigger event includes at least one of the patient eating, the patient resting, a threshold temperature of the patient, a directional orientation of the patient, a change in the patient's weight, a change in the patient's tissue impedance, manual activation by the patient or other human, and a blood chemistry change in the patient.

* * * * *